United States Patent [19]

Gribble

[11] Patent Number: 4,866,076

[45] Date of Patent: Sep. 12, 1989

[54] BIOLOGICALLY ACTIVE COMPOUNDS

[75] Inventor: Andrew D. Gribble, Knebworth, England

[73] Assignee: Smith Kline & French Laboratories Limited, Welwyn Garden City, England

[21] Appl. No.: 222,484

[22] Filed: Jul. 21, 1988

[30] Foreign Application Priority Data

Jul. 22, 1987 [GB] United Kingdom ............... 8717374

[51] Int. Cl.$^4$ ................... A61K 31/47; C07D 217/04
[52] U.S. Cl. ................................ 514/307; 546/143; 546/147; 514/310
[58] Field of Search ............... 546/143, 147; 514/307, 514/310

[56] References Cited

U.S. PATENT DOCUMENTS

| | | | |
|---|---|---|---|
| 4,443,477 | 4/1984 | Witte et al. | 544/390 |
| 4,536,510 | 8/1985 | Wasserman et al. | 514/308 |
| 4,616,086 | 10/1986 | Witte et al. | 544/383 |
| 4,812,573 | 3/1989 | Durant et al. | 546/147 |

FOREIGN PATENT DOCUMENTS

| | | |
|---|---|---|
| 0194548 | 3/1986 | European Pat. Off. . |
| 0201735 | 4/1986 | European Pat. Off. . |
| 0226346 | 11/1986 | European Pat. Off. . |

*Primary Examiner*—Glennon H. Hollrah
*Assistant Examiner*—James H. Turnipseed
*Attorney, Agent, or Firm*—Edward T. Lentz; Janice E. Williams; Alan D. Lourie

[57] ABSTRACT

The invention provides a class of sulphonamide-containing tetrahydroisoquinolinyl compounds having thromboxane antagonist activity.

20 Claims, No Drawings

BIOLOGICALLY ACTIVE COMPOUNDS

The present invention relates to a class of tetrahydroisoquinoline compounds containing a sulphonamido group which have activity as thromboxane $A_2$ antagonists, to the use of the compounds in medicine, to pharmaceutical compositions containing them and to methods for their preparation.

Thromboxane $A_2$ ($TXA_2$) is a potent vasoconstricting and platelet aggregating agent which is formed in platelets and other tissues as a product of the "arachidonic acid cascade". $TXA_2$ produced by the thromboxane synthetase catalysed conversion of prostaglandin $H_2$ ($PGH_2$) which in turn is produced, via the intermediacy of prostaglandin $G_2$ ($PGG_2$), by the action of cyclooxygenase on arachidonic acid. The potency of $TXA_2$ is such that the very small amounts can trigger serious biological consequences and it has been implicated in mediating pathophysiological actions in severe disorders such as circulatory shock and myocardial ischaemia.

One method of inhibiting the effects of thromboxane $A_2$ is through the selective antagonism of $TXA_2/PGH_2$ at the receptor level and various compounds have been reported as $TXA_2$ receptor antagonists, see for example U.S. 4,536,510 and EP 31954.

It has now been discovered that a class of sulphonamide-substituted isoquinolines has biological activity indicative of an ability to antagonise $TXA_2$ receptors. Accordingly, in a first aspect, the present invention provides compounds of the formula (I):

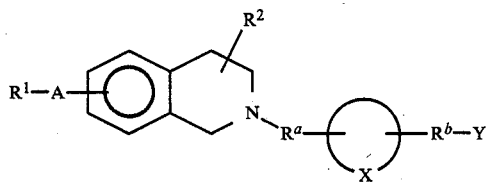

and salts thereof;
wherein
A is a group $NR^3SO_2$ or $SO_2NR^3$;
$R^a$ is an acyclic hydrocarbon group having from 1 to 4 linear carbon atoms;
$R^b$ is a bond or an acyclic hydrocarbon group having from 1 to 3 linear carbon atoms, provided that the total number of linear carbon atoms in $R^a$ and $R^b$ taken together does not exceed four and that the carbon atom in $R^a$ which is adjacent to the isoquinoline ring nitrogen atom is saturated;
the group

is a monocyclic group having between three and seven ring members and containing up to three heteroatoms;
Y is $CO_2H$ or a group hydrolysable to $CO_2H$;
$R^1$ is phenyl optionally substituted by one or more substituents chosen from the group comprising halogen, $C_{1-4}$alkyl, $C_{1-6}$acyl, $C_{1-4}$alkoxy, nitro and trifluoromethyl;
$R^2$ is hydrogen or one or more $C_{1-4}$alkyl substituents located at the 1, 3 and 4 positions of the isoquinoline ring; and
$R_3$ is hydrogen or $C_{1-6}$alkyl.

By linear carbon atoms is meant to those carbon atoms extending in an unbranched chain between the nitrogen atom of the isoquinoline ring and the monocyclic group, and between the monocyclic group and the group Y.

The acyclic hydrocarbon groups $R^a$ and $R^b$ can be alkylene groups, or they can contain alkene and/or alkyne groups. Each group can be a straight chain or branched and any one or more of the linear carbon atoms can be substituted by an alkyl group or groups. Preferably any such alkyl substituents are methyl groups. It is preferred that $R^a$ is an alkylene group and it is particularly preferred that the alkylene group is methylene. $R^b$ suitably is a bond or an alkylene group but preferably it is a bond.

The group A can be located at any one of the aromatic 5-, 6-, 7- or 8-positions of the isoquinoline ring. Preferably the group A is a group $NR^3SO_2$ and particularly it is located at the 7-position of the isoquinoline ring.

The monocyclic group can be a fully saturated, partly unsaturated or aromatic group.

Preferably the monocyclic group is other than a non-aromatic nitrogen-containing heterocycle or an aromatic heterocycle containing more than two nitrogen atoms.

Suitably the monocyclic group is carbocyclic or contains a single heteroatom. Examples of heteroatoms are nitrogen, oxygen and sulphur, a particular example being oxygen.

Particular monocyclic groups are those having five or six ring members, for example aromatic or heteroatomic groups such as phenylene, pyridine or furan groups.

When the monocyclic group is a phenylene group it can be ortho-, meta- or para-phenylene and preferably it is meta-phenylene.

When the monocyclic group is a furan group, the groups $R^a$ and $R^b$ can each be linked either α- or β- to the oxygen atom. Preferably both groups $R^a$ and $R^b$ are linked α- to the oxygen atom.

When the monocyclic group is a pyridine group, the groups $R^a$ and $R^b$ can each be linked α- β- or γ- to the nitrogen. One particular pyridine group is a pyridine ring in which $R^a$ is linked α- to the nitrogen atom and $R^b$ is linked γ- to the nitrogen atom.

When the monocyclic group is phenylene, pyridine or a furan group, suitably the group $R^a$ is $CH_2$ and $R^b$ is a bond.

The monocyclic group can also be a saturated carbocyclic or heterocyclic group, for example cycloalkanes such as cyclopropyl, cyclobutyl, cyclopentyl and cyclohexyl, and monoheterocyclic rings such as tetrahydrofuran and tetrahydrothiophen.

The group Y hydrolysable to $CO_2H$ suitably is a nitrile, amide or ester, for example a $C_{1-4}$alkoxycarbonyl group such as ethoxycarbonyl or methoxycarbonyl, or a carbamoyl, mono-$C_{1-6}$alkylcarbamoyl or di-$C_{1-6}$alkylcarbamoyl group such as N-methylaminocarbonyl and N,N-dimethylaminocarbonyl.

Suitably $R^1$ represents a phenyl group having up to two substituents. Preferably there is only a single substituent. Preferred positions of substitution are the 3- and 4-positions of the phenyl ring.

Examples of $C_{1-6}$acyl substituents are $C_{1-6}$alkanoyl, $C_{1-6}$alkoxycarbonyl and carbamoyl.

Particular examples of the group $R^1$ are unsubstituted phenyl or phenyl substituted by chloro, bromo, methyl, trifluoromethyl and methoxy, a most particular example being phenyl substituted with chloro.

Examples of the group $R^2$ are hydrogen, methyl and ethyl, particularly hydrogen.

Suitably $R^3$ is hydrogen or methyl, particularly hydrogen.

One particular group of compounds of the present invention is represented by the general formula (II):

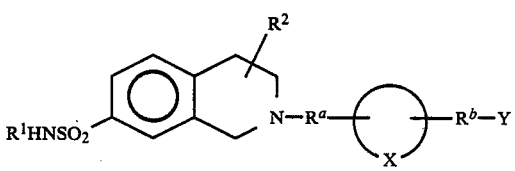
(II)

wherein $R^1$, $R^2$, $R^a$, $R^b$ and

are as defined above.

Particular and preferred groups $R^a$, $R^b$,

, $R^1$ and $R^2$ for compounds of the formula (II) are as defined above in respect of compounds of the formula (I).

Preferred compounds of the present invention are 3-[[7-(3-chlorophenylaminosulphonyl)-1,2,3,4-tetrahydroisoquinolin-2-yl]methyl]benzoic acid and 5-[[7-(3-chlorophenylaminosulphonyl)-1,2,3,4-tetrahydroisoquinolin-2-yl]methyl]-2-furanoic acid, and salts thereof.

Compounds of the formula (I) can form several different types of salt but preferred salts are acid addition salts, formed by interaction of the nitrogen atom of the isoquinoline ring with an appropriate proton acid, and carboxylate salts formed by interaction of the carboxylic acid group with an appropriate base. Compounds of the formula (I) can exist in zwitterionic form and such forms are also within the scope of this invention.

Examples of acid addition salts are those formed by interaction of a compound of the formula (I) with an acid selected from hydrochloric, sulphuric, phosphoric, acetic, methanesulphonic, ethanesulphonic, isethionic, glucuronic, lactobionic, toluenesulphonic, benzenesulphonic, naphthalenesulphonic, hydrobromic, tartaric, citric, maleic, lactic, and camphorsulphonic acids.

Examples of carboxylate salts are alkali metal, alkaline earth metal and ammonium salts. Alkali and alkaline earth metal salts typically are formed by interaction of a carboxylic acid with a metal alkoxide or hydroxide whereas ammonium salts typically are formed by interaction of the carboxylic acid with the appropriate amine or the appropriate ammonium hydroxide.

It is preferred that the salts are pharmaceutically acceptable, although non-pharmaceutical salts are also within the scope of the invention. Such salts can be converted into pharmaceutically acceptable salts or into the corresponding free base or free acid.

Compounds of formula (I) can also exist as solvates, for example hydrates and alcoholates, and all such forms are within the scope of the invention.

Compounds of the formula (I) wherein Y is $CO_2H$ or a $C_{1-4}$alkoxycarbonyl group such as ethoxycarbonyl have activity as thromboxane-$A_2$ receptor antagonists. Compounds of the formula (I) wherein Y is a group hydrolysable to $CO_2H$ are primarily useful as chemical intermediates, unless metabolised by mammals to compounds wherein Y is $CO_2H$ in which case they can function as pro-drugs.

Compounds of the formula (I) can be prepared by the reaction of a compound of the formula (III):

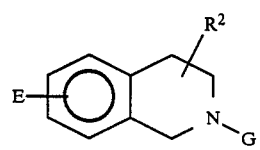
(III)

wherein
E is amino or a group $SO_2L$;
$R^2$ is as defined above;
G is an amine-protecting group or a group

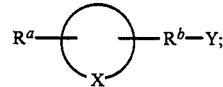

and
L is a leaving group;
with a compound of the formula $R^1M$ wherein M is amino or a group $SO_2L$, provided that one of E and M is $SO_2L$ and the other is amino; and when G is an amine-protecting group removing this and reacting the compound thus formed with an alkylating agent suitable for introducing the group

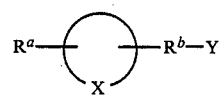

and thereafter, where necessary, hydrolysing Y to give $CO_2H$.

Examples of leaving groups L are the halogens, particularly chlorine.

Typically the amine-protecting group is an acyl group, for example the acyl residue of a $C_{1-6}$alkanoic acid or optionally substituted benzoic acid. A particular protecting group is acetyl.

The alkylating agent typically is a compound of the formula:

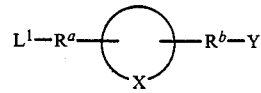

wherein $L^1$ is a leaving group such as halogen, particularly bromine.

The reaction of compounds of the formula (III) with compounds of the formula $R^1M$ suitably is conducted in a polar solvent, usually aprotic and preferably dry, such as dry acetone or dichloromethane, with heating where required, for example at the reflux temperature of the solvent. The reaction typically is conducted in the presence of another base such as pyridine or a trialkylamine such as triethylamine.

Alternatively the reaction can be carried out under Schotten-Baumann conditions e.g. in the presence of an aqueous base such as sodium hydroxide.

Compounds of the formula (III) where E is $SO_2L$ can be prepared from compounds of the formula (IV):

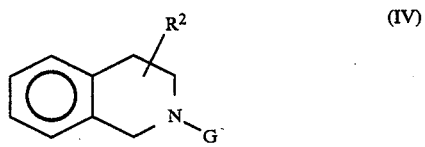

(IV)

according to known methods or methods analogous thereto, see for example European patent application No. 0038177.

Thus, for example, a chlorosulphonyl group can be introduced into the 7-position of a compound of the formula (IV) by reaction with chlorosulphonic acid in a halocarbon solvent such as dichloromethane. When it is required to introduce as chlorosulphonyl group in a position other than the 7-position, this can suitably be achieved by forming the appropriate mercaptotetrahydroisoquinoline and then reacting it with chlorine in glacial acetic acid.

Compounds of the formula (III) wherein E is amino can be prepared according to methods described in European patent application No. 0049135.

When the product of the reaction between compounds of the formula (III) and $R^1M$ is a compound wherein G is an amine-protecting group, the protecting group is removed by methods known per se; for example when G is acetyl, it can be removed by heating with hydrochloric acid in an alkanol such as n-BuOH suitably at the reflux temperature of the solvent mixture.

The reaction of the resulting tetrahydroisoquinoline with an alkylating agent suitably is conducted in a polar solvent such as an alkanoyl, e.g. ethanol; acetonitrile, dimethylformamide or tetrahydrofuran. Typically, the reaction is carried out in the temperature range from 0° C. to 100° C., for example at room temperature to 60° C.

Optionally a second base can be employed, for example a trialkylamine such as triethylamine, or pyridine, or an alkali metal carbonate or bicarbonate such as potassium carbonate and sodium carbonate.

When the group Y is a group hydrolysable to $CO_2H$, the hydrolysis conditions employed will depend upon the precise nature of the group but generally the hydrolysis is achieved by treating with either an aqueous mineral acid such as hydrochloric or sulphuric acids or an alkali such as sodium hydroxide, with heating as required.

Compounds of the formula:

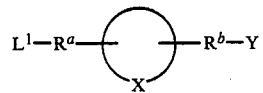

can be prepared according to known methods or methods analogous thereto. For example, compounds wherein

is an aromatic ring such as a benzene ring, $R^a$ is $CH_2$ and $L^1$ is bromine or chlorine, can be prepared by bromination or chlorination of the corresponding compound wherein $L^1$ is hydrogen by reaction with N-bromosuccinimide (NBS) or N-chlorosuccinimide (NCS) in tetrachloromethane. Alternatively, compounds wherein

is an aromatic ring, $R^a$ is $CH_2$ and $L^1$ is chlorine can be prepared by a conventional chloromethylation procedure.

Compounds wherein $L^1$ is halogen can also be prepared from the corresponding compound wherein $L^1$ is hydroxy, according to standard methods, e.g. by reaction with thionyl chloride.

It will be appreciated that when the group G in a compound of the formula (III) is an amine-protecting group, the removal of this group, following the reaction of the formula (III) with a compound $R^1M$, gives rise to an intermediate compound of the formula (V):

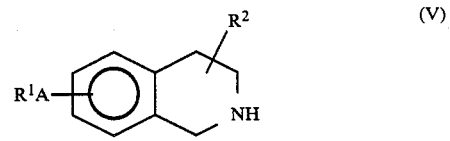

(V)

which can then subsequently be alkylated as described above.

Intermediate compounds of the formula (V) can also be prepared by the reduction of compounds of the formula (VI):

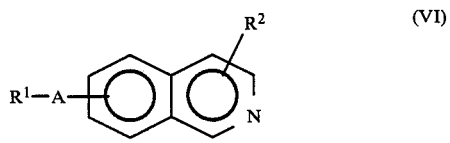

(VI)

for example by hydrogenation over a transition metal catalyst, e.g. as described in European patent application EP 266 949.

Compounds of the formula (I) are useful in the treatment of diseases in which $TXA_2$ is a factor. Thus they would be useful in the treatment of disorders in which aggregation of blood platelets and vasoconstriction play a part.

Particular clinical indications in which the present compounds would be of interest include the treatment or management of post myocardial infarction, coronary thromboses (e.g. in combination with tissue plasminogen activator and other thrombolytics), unstable angina, transient ischaemia, coronary artery bypass grafts, cardiac valve replacement and peripheral and vascular grafts including for example renal transplants.

The compounds of the formula (I) can be administered as the pure compound but it is more usual to administer them as part of a pharmaceutical composition in association with a carrier and one or more excipients. In a further aspect, therefore, the present invention provides a pharmaceutical composition comprising a compound of the formula (I) and a pharmaceutically acceptable carrier.

The compositions can be administered in standard manner, for example orally, parenterally, transdermally, rectally, via inhalation or via buccal administration.

Compounds of formula (I) and their pharmaceutically acceptable salts which are active when given orally or via buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil. Such compositions can be administered for example by bolus injection or infusion.

A typical suppository formulation comprises a compound of formula (I) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

Each such dosage unit suitably contains from 1 mg to 1 g, preferably from 5 mg to 500 mg, e.g. 100 mg or 200 mg, of a compound of the formula (I) or a pharmaceutically acceptable salt thereof calculated as the compound itself.

A typical daily dosage regimen is 10 mg to 1 g for an average human weighing approximately 70 kg, administered in 1 to 4 dosage units, preferably 1 or 2.

The compositions of this invention, in addition to containing a compound of the formula (I) can also contain other agents: for example one or more agents chosen from phosphodiesterase inhibitors, hypolipidemic agents, platelet aggregation inhibitors, vasodilators, β-adrenergic receptor blockers, ACE inhibitors, tissue plasminogen activator and other thrombolytics, and antiarrhythmics.

The compositions of the present invention are prepared by bringing the active constituent into association with a pharmaceutically acceptable carrier and optionally other excipients and ingredients as defined above.

As indicated above, compounds of the formula (I) have biological activity that is indicative of an ability to antagonise $TXA_2$ receptors. The biological activity has been demonstrated in the human platelet binding assay.

The platelet binding assay used was essentially the method described by Mais et al, *J. Pharm. Exp. Ther.*, 1985, 235(3), 729–734 where [$^{125}$I]PTA-OH was used as the receptor ligand.

The $IC_{50}$ values represent the concentration which produces a 50% inhibition of specific [$^{125}$I]PTA-OH binding.

The activities of the compounds of the present invention are described in Example 7.

The following Examples are illustrative of the invention.

In the Examples, all temperatures are in °C. Melting points are uncorrected and were obtained in an open capillary tube using a Büchi 510 Melting Point Apparatus.

EXAMPLE 1

To a mixture of 7-(3-chlorophenylsulphamoyl)-1,2,3,4-tetrahydroisoquinoline hydrochloride (1.8 g, 5 mmol) and triethylamine (0.51 g, 5 mmol) in dry acetonitrile (25 ml), heated to 70° C., was added half of a solution of methyl-2-(bromomethyl)benzoate (1.15 g, 5 mmol) and triethylamine (0.51 g, 5 mmol) in acetonitrile (25 ml) over 0.5 hr. After 1.5 hr, the remainder of the solution was added slowly over 2 hr and stirred for a further 1 hr. After cooling and filtration the concentrated filtrate was chromatographed (silica gel, ether) to give a methyl-2-[[7-(3-chlorophenylsulphamoyl)-1,2,3,4-tetrahydroisoquinolin-2-yl]methyl]benzoate (0.66 g, 28%) as an oil. To this, in methanol (30 ml), was added 15% sodium hydroxide solution (8 ml) and the mixture was stirred for 3 hr. The solvent was removed in vacuo, water was added and the pH was adjusted to 6 with 2N HCl to give, after recrystallisation from IPA, 2-[[7-(3-chlorophenylsulphamoyl)-1,2,3,4-tetrahydroisoquinolin-2-yl]methyl]benzoic acid, $H_2O$, 0.6HCl, 0.48$(CH_3)_2$CHOH.

$C_{23}H_{21}ClN_2O_4S.H_2O$, 0.6HCl, 0.48$(CH_3)_2$CHOH: Found: C 56.07, H 4.97, N 5.29, S 5.62, Cl 10.86. Requires: C 55.77, H 5.27, N 5.32, S 6.09, Cl 10.82.

Following the procedure of Example 1, substituting methyl-3-(bromomethyl)benzoate and methyl-4-(bromomethyl)benzoate for methyl-2-(bromomethyl)benzoate, gave respectively:

EXAMPLE 2

3-[[7-(3-Chlorophenylsulphamoyl)-1,2,3,4-tetrahydroisoquinolin-2-yl]methyl]benzoic acid, 0.25H$_2$O. m.pt. 174°–176° C.

C$_{23}$H$_{21}$ClN$_2$O$_4$S.0.25H$_2$O: Found: C 59.66, H 4.61, N 6.06, Cl 7.91. Requires: C 59.85, H 4.70, N 6.07, Cl 7.68. and

EXAMPLE 3

4-[[7-(3-Chlorophenylsulphamoyl)-1,2,3,4-tetrahydroisoquinolin-2-yl]methyl]benzoic acid, 0.25C$_2$H$_5$OH, 0.19H$_2$O (from ethanol). m.pt. 226°–230° C.

C$_{23}$H$_{21}$ClN$_2$O$_4$S.0.25C$_2$H$_5$OH, 0.19H$_2$O: Found: C 59.85, H 4.69, N 6.02, S 6.78, Cl 7.66. Requires: C 59.84, H 4.85, N 5.96, S 6.83, Cl 7.55.

EXAMPLE 4

Following the procedure of Example 1 to methyl-2-[[7-(3-chlorophenylsulphamoyl)-1,2,3,4-tetrahydroisoquinolin-2-yl]methyl]benzoate, substituting methyl-5-(chloromethyl)-2-furoate (1.75 g, 10 mmol) for methyl-2-(bromomethyl)benzoate and using corresponding proportions of other reagents, gave methyl-5-[[7-(3-chlorophenylsulphamoyl)-1,2,3,4-tetrahydroisoquinolin-2-yl]methyl]-2-furoate (2.86 g, 62%), m.pt. 167°–168° C. (from methanol).

C$_{22}$H$_{21}$ClN$_2$O$_5$S: Found: C 57.58, H 4.35, N 6.01, Cl 7.95, S 7.38. Requires: C 57.33, H 4.59, N 6.08, Cl 7.69, S 6.96.

EXAMPLE 5

The compound of Example 4 (2 g) was treated with 10% sodium hydroxide solution (30 ml) in methanol (200 ml) for 1.5 hr. The mixture was concentrated, water added and the pH adjusted to 6 with HCl, to give, after recrystallisation from methanol-water, 5-[[7-(3-chlorophenylsulphamoyl)-1,2,3,4-tetrahydroisoquinolin-2-yl]methyl]-2-furoic acid, H$_2$O, 0.2CH$_3$OH (1.17 g, 57%) m.pt. 176°–178° C.

C$_{21}$H$_{19}$ClN$_2$O$_5$S.H$_2$O, 0.2CH$_3$OH: Found: C 53.97, H 4.61, N 5.91, Cl 7.96, S 6.54. Requires: C 54.02, H 4.66, N 5.94, Cl 7.52, S 6.80.

EXAMPLE 6

(a) To a refluxing mixture of ethylisonicotinate (30.2 g, 0.2 mol), and concentrated sulphuric acid (19.6 g, 0.2 mol) in methanol (180 ml) was added, with stirring over 1 hr, a solution of ammonium persulphate (91.3 g, 0.4 mol) in water (14 ml). Reflux was continued for 8 hr and then the methanol was removed in vacuo, the pH was adjusted to ca. 7–8 with sodium hydroxide, and the mixture was extracted with chloroform (4×200 ml). The extracts were dried (MgSO$_4$), concentrated and subjected to chromatography (silica gel, ether) to give an approximate 2:1 mixture of ethyl- and methyl-2-(hydroxymethyl)isonicotinate (6.23 g, ca. 17%) as a yellow solid. To this mixture (5.5 g, ca. 30 mmol) in chloroform (75 ml) cooled to 0° C. was added dropwise a solution of thionylchloride (11.42 g, 96 mmol) in chloroform (25 ml). After 1 hr, the solution was concentrated to give an oil which was triturated with ether. The resulting solid was recrystallised from isopropanol to give an approximate 2:1 mixture of ethyl- and methyl-2-(chloromethyl)isonicotinate hydrochloride (4 g, 58%).

(b) Following the procedure of Example 1, substituting the compound of Example 6(a) for methyl-2-(bromomethyl)benzoate, and using corresponding proportions of the other reagents, (with the exception that one more equivalent of triethylamine was introduced to account for this compound being a hydrochloride salt) gave 2-[[7-(3-chlorophenylsulphamoyl)-1,2,3,4-tetrahydroisoquinolin-2-yl]methyl]isonicotinic acid hydrochloride (from methanol-ether) m.pt. >240° C.

C$_{22}$H$_{20}$ClN$_3$O$_4$S.1.12HCl, 0.4H$_2$O: Found: C 52.23, H 4.21, N 8.18, S 6.40, Cl 14.86. Requires: C 52.22, H 4.36, N 8.30, S 6.34, Cl 14.88.

EXAMPLE 7

Biological Activity

The compounds of Examples 1 to 6 were tested in the human platelet binding assays as described above and the results obtained are shown in the Table below:

| Compound of Example No. | Human Platelet Binding IC$_{50}$(μm) |
| --- | --- |
| 1 | 2.6 |
| 2 | 0.5 |
| 3 | 4.0 |
| 4 | 5.0 |
| 5 | 0.76 |
| 6 | 2.9 |

What is claimed is:

1. A compound of the formula (I):

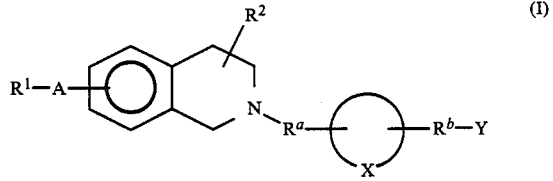

and salts thereof; wherein

A is a group NR$^3$SO$_2$ or SO$_2$NR$^3$;

R$^a$ is an acyclic hydrocarbon group having from 1 to 4 linear carbon atoms;

R$^b$ is a bond or an acyclic hydrocarbon group having from 1 to 3 linear carbon atoms, provided that the total number of linear carbon atoms in R$^a$ and R$^b$ taken together does not exceed four and that the carbon atom in R$^a$ which is adjacent to the isoquinoline ring nitrogen atom is saturated;

the group

is a monocyclic group having between three and seven ring members and containing up to three heteroatoms;

Y is CO$_2$H or a group hydrolysable to CO$_2$H;

R$^1$ is phenyl optionally substituted by one or more substituents chosen from the group consisting of halogen, C$_{1-4}$alkyl, C$_{1-6}$acyl, C$_{1-4}$alkoxy, nitro and trifluoromethyl;

R$^2$ is hydrogen or one or more C$_{1-4}$alkyl substituents located at the 1, 3 and 4 positions of the isoquinoline ring; and R$^3$ is hydrogen or C$_{1-6}$alkyl.

2. A compound according to claim 1 wherein A is a group $NR^3SO_2$.

3. A compound according to claim 1 wherein Y is $CO_2H$ or a $C_{1-4}$alkyl ester thereof.

4. A compound according to claim 1 wherein $R^3$ is hydrogen.

5. A compound according to claim 1 wherein $R^1$ is chosen from unsubstituted phenyl or phenyl substituted with chloro, bromo, methyl, trifluoromethyl or methoxy.

6. A compound according to claim 5 wherein $R^1$ is phenyl bearing a single substituent which is 3-chloro.

7. A compound according to claim 1 wherein

is selected from phenylene, pyridine or a furan group.

8. A compound according to claim 7 wherein $R^a$ is $CH_2$ and $R^b$ is a bond.

9. A compound according to claim 7 wherein the phenylene group is meta phenylene.

10. A compound according to claim 1 having the formula (II):

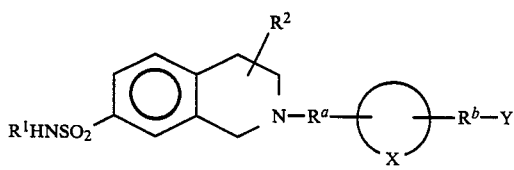

wherein $R^1$, $R^2$, $R^a$, $R^b$ and

are as defined in claim 1.

11. A compound according to claim 10 wherein Y is $CO_2H$ or a $C_{1-4}$alkyl ester derivative thereof.

12. A compound according to claim 10 wherein $R^1$ is chosen from unsubstituted phenyl or phenyl substituted with chloro, bromo, methyl, trifluoromethyl or methoxy.

13. A compound according to claim 12 wherein $R^1$ is phenyl bearing a single substituent which is 3-chloro.

14. A compound according to claim 10 wherein

is phenylene, pyridine or a furan group.

15. A compound according to claim 14 wherein $R^a$ is $CH_2$ and $R^b$ is a bond.

16. A compound according to claim 14 wherein the phenylene group is meta phenylene.

17. A compound selected from
3-[[7-(3-chlorophenylaminosulphonyl)-1,2,3,4-tetrahydroisoquinolin-2-yl]methyl]benzoic acid;
5-[[7-(3-chlorophenylaminosulphonyl)-1,2,3,4-tetrahydroisoquinolin-2-yl]methyl]-2-furanoic acid, and salts thereof.

18. A pharmaceutical composition comprising a therapeutically effective but non-toxic amount of a compound as defined in claim 3, and a pharmaceutically acceptable carrier.

19. A pharmaceutical composition comprising a therapeutically effective but non-toxic amount of a compound as defined in claim 11, and a pharmaceutically acceptable carrier.

20. A method of treatment of thromboxane $A_2$ mediated diseases in a mammal, which method comprises administering to said mammal a non-toxic but effective thromboxane $A_2$ antagonist amount of a compound as defined in claim 3.

* * * * *